United States Patent [19]

Liu et al.

[11] Patent Number: 4,873,336

[45] Date of Patent: Oct. 10, 1989

[54] PROCESS FOR THE PREPARATION OF N-VINYL LACTAMS

[75] Inventors: Kou-Chang Liu, Wayne; Paul D. Taylor, West Milford, both of N.J.

[73] Assignee: GAF Corporation, Wayne, N.J.

[21] Appl. No.: 183,559

[22] Filed: Mar. 28, 1988

[51] Int. Cl.$^4$ ............... C07D 207/267; C07D 211/74; C07D 223/00
[52] U.S. Cl. .................................. 546/243; 548/543; 548/552; 540/604
[58] Field of Search ....................... 548/543, 552, 243; 540/604

[56] References Cited

U.S. PATENT DOCUMENTS 2,317,804  4/1943  Reppe et al. ..................... 546/243
3,249,625  5/1966  Bestian et al. ................... 546/243

*Primary Examiner*—David B. Springer
*Attorney, Agent, or Firm*—Marilyn J. Maue; Joshua J. Ward

[57] ABSTRACT

The invention relates to the preparation of N-vinyl lactams having the formula

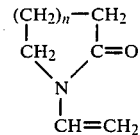

wherein n is an integer having an value of from 1 to 3 in a one-stage, non-aqueous process which comprises reacting a lactam having the formula

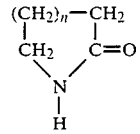

with acetylene under an acetylene partial pressure of from about 25 to about 125 psig. in the presence of an inert gas diluent and a catalyst having the formula

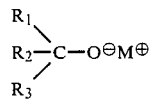

wherein $R_1$, $R_2$ and $R_3$ are all lower alkyl or alyl or one of $R_1$, $R_2$ and $R_3$ can also be hydrogen and M is a metal selected from the group of cesium, potassium, sodium and lithium.

16 Claims, No Drawings

PROCESS FOR THE PREPARATION OF N-VINYL LACTAMS

BACKGROUND OF THE INVENTION

Prior processes for the preparation of vinyl lactams are generally carried out in two-stages where, in the first stage, potassium hydroxide is reacted with the lactam to produce the corresponding lactam salt catalyst and water followed by vinylation of lactam with acetylene in the presence of the salt catalyst in the second stage to produce the desired vinylated product. This process is hampered by the formation of potassium 4-aminobutyrate by-product caused by lactam ring opening unless great care is taken to prevent its formation by removal of water during the reaction and by employing a sterically hindered alkoxide so as to prevent ring opening. Ring opening destroys the catalyst and the process looses catalytic activity; thus for all intents and purposes this should be avoided.

Accordingly, it is an object of the present invention to obviate the above difficulty by a commercially feasible and economical process.

Another object of the invention is to produce a vinylpyrrolidone containing essentially no metal amino butyrate by-product.

Another object is to prevent catalyst ring opening and consequent loss of reaction activity.

Still another object is to eliminate costly removal of water in the preparation of a catalyst for synthesis of N-vinyl lactams.

These and other objects of the invention will become apparent from the following description and disclosure.

THE INVENTION

According to this invention there is provided a non-aqueous liquid phase process for the preparation of an N-vinyl lactam which is effected in a single stage reaction. The reaction comprises contacting with acetylene under between about 25 and about 125 psig. acetylene partial pressure preferably in the presence of an inert gas diluent and a catalyst having the formula

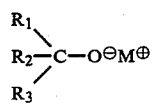

wherein each of $R_1$, $R_2$ and $R_3$ are alkyl groups of from 1 to 4 carbon atoms or aryl or one of $R_1$, $R_2$ and $R_3$ is hydrogen and M is an alkali metal, preferably a metal selected from the group of potassium, sodium and lithium.

If desired, an acetylene diluent can be employed at a concentration of between about 25 and about 200 wt. % of the total reaction mixture. The diluent, when used, can be selected from any one of the inert gases such as nitrogen, helium, argon, krvoton, methane, ethane, propane, or mixtures thereof.

The lactam reactants of this invention are those having the formula

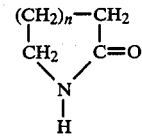

wherein n has a value of from 1 to 3 and can be branched or linear. Of these, 2-pyrrolidone and caprolactam are preferred and 2-pyrrolidone is most preferred. The catalysts of the present invention wherein $R_1$, $R_2$ and $R_3$ represent methyl or ethyl groups and M is potassium or sodium are most effective. Of this group, potassium t-butoxide is conveniently useful. The catalyst is employed in a molar ratio of from about 1:20 to about 1:200, more desirably from 1:60 to 1:100, based on lactam.

The reaction is generally effected at a temperature between about 125° C. and 185° C. for a period of from about 2 to about 20 hours, preferably at a temperature of from about 135° C. to about 165° C. for a period of about 5 to 15 hours. Under optimum conditions, the system is pressurized with between about 70 and about 110 psig. of acetylene and between about 25 and about 200 psig. of inert gas diluent. More often the inert gas is employed at a partial pressure of from about 60 to about 125 psig.

A main advantage of the present process is that a sterically hindered alkanol is produced instead of the water generated during catalyst preparation. Sterically hindered tertiary and secondary alkanols cause no ring opening of the lactam reactant, thus obviating the need for a tedious and separate catalyst preparation step in the process.

The product of the process can be produced in yields above 90% if desired depending upon the pressure employed and the reaction time.

Having generally described the invention, reference is now had to the accompanying Examples of which Examples 1 and 4 illustrate preferred embodiments of the invention and Examples 2 and 3 are presented for comparative purposes. These Examples should in no way be construed as limiting to the scope of the invention as more broadly described above and in the appended claims.

EXAMPLE 1

Into a 1 liter stainless steel autoclave was charged 628 g. (7.4 moles) of 2-pyrrolidone and 12.6 g. (0.11 mole) of potassium t-butoxide. The autoclave was purged three times with nitrogen at room temperature and then heated to 160° C. Acetylene (partial pressure 100 psig.) was added and the solution was agitated at a speed of 1800 rpm. After 8 hours of vinylation, a 62% conversion with 90% selectivity to N-vinyl pyrrolidone was obtained.

EXAMPLE 2

Into a 1 liter stainless steel autoclave was charged 628 g. (7.4 moles) of 2-pyrrolidone and 7.4 g., 0.11 moles of 85% potassium hydroxide pellets. This mixture was vinylated with acetylene under the same conditions of temperature and pressure as employed in Example 1. After 8 hours of reaction, less than 5% of N-vinyl pyrrolidone was obtained.

EXAMPLE 3

Into a 1 liter stainless steel autoclave was charged 628 g. (7.4 moles) of 2-pyrrolidone and 12.6 g. (0.11 mole) of potassium t-butoxide. The autoclave was purged three times with nitrogen at room temperature after which 100 pounds of nitrogen was added, the temperature was raised to 160° C. and the pressure of nitrogen was adjusted to 100 psig. and acetylene (100 psig) was added. The solution is agitated at a speed of 1800 rpm. After 8 hours of vinylation, about 50% yield of N-vinyl pyrrolidone was obtained.

EXAMPLE 4

2-pyrrolidone (628 g., 7.47 moles) was charged into a 1 liter four neck round bottom flask equipped with a condenser, mechanical stirrer, thermometer and nitrogen inlet, and heated to 90° C. Potassium hydroxide (7.4 g., 85% pellet, 0.11 moles) was added. The solution was held at 90° C. and 0.1 mm Hg pressure for 1 hour to remove water from the solution. This solution was then transferred into a 1 liter stainless steel autoclave and vinylated with acetylene under the same conditions of temperature and pressure as employed in Example 1. After 8 hours of reaction, 75% conversion with 90% selectivity to N-vinyl pyrrolidone was obtained.

EXAMPLE 5

Continuous Process

Into a nitrogen purged 1 liter stainless steel sealed reactor is charged 628 g. of 2-pyrrolidone and 12 g. of sodium t-butoxide catalyst. The reactor is then heated to 150° C. and acetylene was added to obtain a partial pressure of 100 psig. Also propane is charged to a partial pressure of 100 psig. The resulting liquid mixture is agitated at 150° C. until about 50% conversion of 2-pyrrolidone to N-vinyl pyrrolidone product takes place. The product mixture is then withdrawn and product and unreacted 2-pyrrolidones are separated by fractional distillation. The N-vinyl-2-pyrrolidone substantially free of contamination is recovered as the product of the process and the 2-pyrrolidone is recycled to the reactor for contact with additional catalyst and acetylene feed.

It will become apparent from the accompanying description and disclosure that many alterations and variations can be made in Examples 1 and 5 without departing from the scope of the invention. For example, any of the t-alkyl metal salt catalysts described herein can be substituted for potassium t-butoxide to provide the same advantages over the reactions set forth in Examples 2 and 3. Also, other diluents such as propane/ethane, or other aforementioned inert gases or mixtures thereof can be substituted for nitrogen or propane to provide the same beneficial effects. Still further, the reaction in Example 1 can be carried out in a continuous process with recycle of unreacted material, if desired.

Having thus described the invention, what is claimed is:

1. A single stage non-aqueous liquid process for the preparation of an N-vinyl lactam which comprises reacting a lactam having the formula

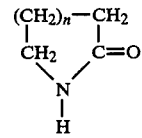

wherein n is an integer having a value of from 1 to 3 with acetylene under an acetylene partial pressure of from about 25 to about 125 psig. in the presence of a catalyst having the formula

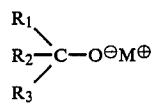

wherein $R_1$, $R_2$ and $R_3$ are each lower alkyl or aryl or wherein one of $R_1$, $R_2$ and $R_3$ is hydrogen and M is an alkali metal.

2. The process of claim 1 wherein said lactam is 2-pyrrolidone and said product is N-vinyl-2-pyrrolidone.

3. The process of claim 1 wherein said lactam is caprolactam and said product is N-vinyl-caprolactam.

4. The process of claim 1 wherein said process is effected in the presence of an inert gas diluent and said inert gas diluent is selected from the group of nitrogen, helium, argon, krypton, propane, ethane and methane and is employed in an amount of from about 25 wt. % to about 200 wt. % of the total reaction mixture.

5. The product of claim 4 wherein said inert gas diluent is employed at a partial pressure of from about 60 psig. to about 125 psig.

6. The process of claim 4 wherein said diluent is nitrogen.

7. The process of claim 4 wherein said diluent is propane.

8. The process of claim 2 wherein M is a metal selected from the group of potassium, sodium, lithium and cesium.

9. The process of claim 8 wherein said catalyst is potassium t-butoxide.

10. The process of claim 8 wherein said catalyst is sodium t-butoxide.

11. The process of claim 1 wherein said process is effected at a temperature of between about 125° C. and about 185° C.

12. The process of claim 11 wherein the process is carried out with agitation over a period of from about 3 to about 20 hours.

13. The process of claim 2 wherein said process is effected at a temperature of between about 135° C. and 165° C. for a period of from about 5 to about 15 hours.

14. The process of claim 2 wherein the partial pressure of acetylene is between about 70 psig. and about 110 psig.

15. The process of claim 14 wherein the reaction is continued until between about 40 wt. % and about 65 wt. % of product is obtained.

16. The process of claim 15 wherein the N-vinyl pyrrolidone product and unreacted pyrrolidone are separated from the product mixture by fractional distillation and the unreacted pyrrolidone is recycled to the reaction for contact with an additional amount of catalyst and acetylene.

* * * * *